United States Patent [19]

Saotome et al.

[11] Patent Number: 4,873,301
[45] Date of Patent: Oct. 10, 1989

[54] OPTICALLY ACTIVE, ETHYLENICALLY UNSATURATED POLYMERS OF AMINO PENICILLANIC ACID COMPOUNDS

[75] Inventors: Yasushi Saotome, Meguro; Takeo Miyazawa, Minato; Takeshi Endo, Yokohama, all of Japan

[73] Assignee: M & D Research Co., Ltd., Tokyo, Japan

[21] Appl. No.: 147,722

[22] Filed: Jan. 25, 1988

[30] Foreign Application Priority Data

Feb. 26, 1987 [JP] Japan .................................. 62-43295

[51] Int. Cl.$^4$ ............................................. C08F 28/06
[52] U.S. Cl. ..................................... 526/257; 540/314
[58] Field of Search .......................................... 526/257

[56] References Cited

FOREIGN PATENT DOCUMENTS 403694 8/1974 U.S.S.R. .

*Primary Examiner*—Christopher Henderson
*Attorney, Agent, or Firm*—Koda and Androlia

[57] ABSTRACT

Disclosed are an optically active, ethylenically unsaturated monomer represented by the following structural formula:

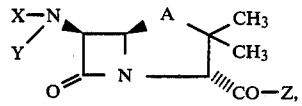

wherein: A stands for S, SO or $SO_2$; X and Y each stand for a hydrogen atom or a substituent selected from the group consisting of alkyl groups and acyl groups; Z stands for a substituent selected from the group consisting of alkoxy, alkylamino, hydroxyl and silyloxy groups; and X and Y can be bonded together to form a ring with the nitrogen atom to which they are bonded or X and Y can be a single group bonded to said nitrogen atom through a double bond, with the proviso that at least one of X and Z is an alkenyl equivalent to said group, and polymers of this monomer. One typical instance of the monomer is benzyl 6-acrylaminopenicillanate.

14 Claims, No Drawings

OPTICALLY ACTIVE, ETHYLENICALLY UNSATURATED POLYMERS OF AMINO PENICILLANIC ACID COMPOUNDS

BACKGROUND OF THE INVENTION (1) Field of the Invention

The present invention relates to a novel optically active monomer and a novel optically active polymeric compound which is a polymer of this optically active monomer. More particularly, the present invention relates to a 6-aminopenicillanic acid derivative having a radical-polymerizable substituent and a polymer prepared by using this derivative as one starting material.

(2) Description of the Related Art

Optically active polymeric compounds are used in various fields. Typical instances of their uses are the use as a catalyst where the specific molecule-recognizing capacity of the optically active molecule is utilized and the use as a filler for chromatography where the asymmetry-discriminating capacity of the optically active molecule is utilized. These uses are described in detail in Collection of Abstracts of Lectures published at the Microsymposium (subtitle: Optially Active Polymers) of The Society of Polymer Science, Japan held on Nov. 25 and 26, 1986, at Kanazawa, Japan.

As the polymeric compounds applied to these uses, various naturally produced natural polymers, chemical derivatives thereof and various synthetic products are known. However, in view of the use as a catalyst wherein the specific molecule-recognizing capacity and the use as a filler wherein the asymmetry-discriminating capacity of the optically active molecule is utilized, presently known optically active polymers do not sufficiently satisfy industrial requirements. Natural polymers and chemical derivatives thereof, as represented by polysaccharides, are easily available, but since they are natural products, polymers having a desired molecular weight cannot be easily obtaied. Needless to say, the molecular weight is an important factor having great influences on the film-forming property and solubility. The synthetic products are disadvantageous, as compared with natural products or derivatives thereof, in that many steps are necessary for the production.

SUMMARY OF THE INVENTION

As pointed out hereinbefore, many optically active polymeric compounds are known, but there is a great demand for novel and improved optically active polymeric compounds. More specifically, the development of optically active polymeric compounds which are easily available and can be produced by simple preparation steps, and in which characteristics such as the molecular weight are variable, and starting materials for the production of these optically active polymeric compounds are desired.

It is a primary object of the present invention to provide a novel optically active monomer and a novel optically active polymer in the production of which the foregoing problems have been overcome. More specifically, the present invention provides a 6-aminopenicillanic acid derivative having a radical-polymerizable substituent on it and an optically active polymer prepared by using this derivative as a sole or one starting material.

The above object and other objects of the present invention have been achieved by providing an optically active monomer which is a modified 6-aminopenicillanic acid that is an easily available culture product or an acylated derivative thereof in that a radical-polymerizable substituent has been introduced thereinto with the optical activity of the penicillanic acid skeleton (hereinafter referred to as "penam nucleus") maintained and also by providing an optically active polymeric compound obtained by radical-homopolymerizing or radical-copolymerizing this monomer as a starting material. That is, the present invention is characterized in that the penam nucleus is used as the optically active site in the optically active monomer and the optically active polymer.

More specifically, in accordance with one aspect of the present invention, there is provided an optically active, ethylenically unsaturated monomer represented by the following structural formula (I):

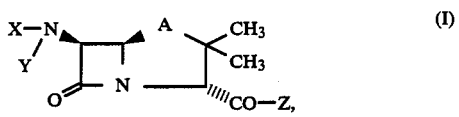

wherein: A stands for S, SO or SO$_2$; X and Y each stand for a hydrogen atom or a substituent selected from the group consisting of alkyl groups and acyl groups; Z stands for a substituent selected from the group consisting of alkoxy, alkylamino, hydroxyl and silyloxy groups; and X and Y can be bonded together to form a ring with the nitrogen atom to which they are bonded, or X and Y can be a single group bonded to said nitrogen atom through a double bond, with the proviso that at least one of X and Z is an alkenyl equivalent to said group.

In accordance with another aspect of the present invention, there is provided an optically active polymer having a number average molecular weight of at least 3,000 and comprising substantially 100 mole% of recurring units formed by cleavage of the ethylenically unsaturated bond of the group X or Z of an optically active, ethylenically unsaturated monomer represented by the following structural formula (I):

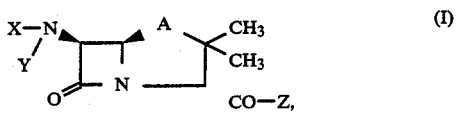

wherein: A stands for S, SO or SO$_2$; X and Y each stand for a hydrogen atom or a substituent selected from the group consisting of alkyl groups and acyl groups; Z stands for a substituent selected from the group consisting of alkoxy, alkylamino, hydroxyl and silyloxy groups; and X and Y can be bonded together to form a ring with the nitrogen atom to which they are bonded, or X and Y can be a single group bonded to said nitrogen atom through a double bond, with the proviso that one of X and Z is an alkenyl equivalent to said group.

According to the present invention, there are provided a 6-aminopenicillanic acid derivative having a radical-polymerizable substituent and an optically active polymer prepared by using this derivative as a starting material. It is expected that a series of compounds provided by the present invention will be applicable to various uses by utilizing the chemical and physical properties thereof, such as a high optical purity.

DETAILED DESCRIPTION OF THE PREFERRED EMBODIMENTS

Optically Active Monomer

Definition of Monomer

The optically active, ethylenically unsaturated monomer (hereinafter referred to as "monomer") of the present invention is represented by the above-mentioned structural formula.

In the structural formula, A, X, Y and Z are as defined above. In the case where X and Y are alkyl or acyl groups, it is preferable that they be of about 1 to about 30, especially about 1 to about 15 carbon atoms. In the case where Z is an alkoxy, alkylamino or silyloxy group, it is preferable that they be of about 1 to about 30, especially about 1 to about 20 carbon atoms. The term "alkyl" herein used as such or in "alkoxy" includes "aralkyl".

The ethylenically unsaturated bond rendering this monomer radical-polymerizable is present in the group X and/or the group Z. That is, this optically active monomer has an ethylenical unsaturation at the 6-position and/or the 3-position of the penam nucleus. In typical monomers of the present invention, a radical-polymerizable group is present at one of the 6- and 3-positions. In the present invention, the term "ethylenically unsaturated bond" is used as the term having the same meaning or being exchangeable with "radical-polymerizable carbon-to-carbon double bond".

The compound of the formula (I) has ethylenical unsaturation by the fact that the substituent X or Z is an alkenyl equivalent. When X is an alkyl, the alkenyl equivalent is an alkenyl, when X is an acyl of a formula RCO— wherein R is an alkyl, the alkenyl equivalent is R'CO wherein R' is a corresponding alkenyl, and when Z is an alkoxy, the alkenyl equivalent is an alkenyloxy.

As the compound having a radical-polymerizable group as mentioned above at the 6-position of the penam nucleus, there can be mentioned a series of compounds in which one nitrogen atom of the amino group at the 6position is substituted with a polymerizable acyl group (X) such as an acryl, methacryl, vinylbenzoyl or cyanoacryl group. In this case, the other hydrogen atom attached to the nitrogen atom need not be substituted (Y=H). In the case where this hydrogen atom is substituted (Y≠H), there can be mentioned, as the substituent, lower alkyl groups such as methyl and ethyl groups, aralkyl groups such as a benzyl group, and acyl groups such as acetyl and benzoyl groups. Furthermore, the nitrogen atom at the 6-position can be included as an amide or imide type nitrogen atom in the ring structure or can be connected to a substituent through a double bond such as a carbon-to-nitrogen double bond. In the case where a polymerizable group is present at the 6-position, the carboxyl group at the 3-position can be unsubstituted (Z=OH) or can be converted to an amide structure such as a carbamoyl or substituted carbamoyl group. Furthermore, the carboxyl group at the 3-position can be an alkyl ester such as a methoxycarbonyl group, a substituted alkyl ester such as a benzyloxycarbonyl group or a metal atom ester structure such as a trialkylsilyloxycarbonyl group. The sulfur atom at the 1-position can be a sulfide sulfur atom or a sulfoxide or sulfone sulfur atom.

As the compound having a radical-polymerizable group at the 3-position of the penam nucleus, there can be mentioned a series of compounds in which the 3-position is an ester structure having a carbon-to-carbon double bond, such as a vinylbenzyloxycarbonyl or 1-(acryloxy)ethoxycarbonyl group. As another example of the compound, there can be mentioned an amide structure such as a vinylcarbamoyl or isopropenylcarbamoyl group. In this case, the hydrogen atom attached to the nitrogen atom at the 6-position may be substituted or unsubstituted. In the case where this hydrogen atom is substituted (X and/or Y≠H), there can be mentioned, as the substituent, lower alkyl groups such as methyl and ethyl groups, aralkyl groups such as a benzyl group, and acyl groups such as acetyl and benzoyl groups. This nitrogen atom can be included as an imide nitrogen or the like in a ring structure or can be connected to the substituent through a double bond such as a carbon-to-nitrogen double bond. Furthermore, the nitrogen atom can be a substituted or unsubstituted ammonium salt. The sulfur atom at the 1-position can be a sulfide sulfur atom, a sulfoxide sulfur atom or a sulfone sulfur atom.

Preferred examples of the optically active, ethylenically unsaturated monomer represented by the above-mentioned structural formula should satisfy at least one, preferably as many as possible, of the following requirements.

(i) X is an acyl group, especially an acryloyl, methacryloyl, phenylacetyl or benzoyl group or hydrogen atom.

(ii) Y is a hydrogen atom.

(iii) Z is an alkoxy group, especially a benzyloxy or vinylbenzyloxy group.

(iv) A is S or SO.

(v) Only one of X and Z has an ethylenically unsaturated bond.

Preferred examples of the optically active, ethylenically unsaturated monomer of the present invention satisfying these requirements are shown in the following Table, in which Ph stands for a phenyl group and Ph' stands for a phenylene group (o-, m- or p-).

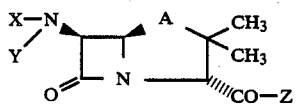

| Name of Compound | A | X | Y | Z |
|---|---|---|---|---|
| (a) benzyl 6-acrylaminopenicillanate | S | CH$_2$=CH—CO— | H— | —O—CH$_2$—Ph |
| (b) benzyl 6-acrylaminopenicillanate sulfoxide | O↑S | CH$_2$=CHCO— | H— | —O—CH$_2$—Ph |

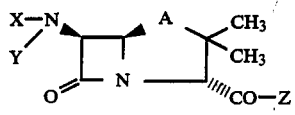

| Name of Compound | A | X | Y | Z |
|---|---|---|---|---|
| (c) benzyl 6-methacrylaminopenicillanate sulfoxide | O↑S | $CH_2=C(CH_3)-CO-$ | H— | —O—CH$_2$—Ph |
| (d) vinylbenzyl 6-phenylacetaminopenicillanate | S | Ph—CH$_2$—CO— | H— | —O—CH$_2$—Ph'—CH=CH$_2$ |
| (e) vinylbenzyl 6-aminopenicillanate | S | H— | H— | —O—CH$_2$—Ph'—CH=CH$_2$ |
| (f) vinylbenzyl 6-aminopenicillanate sulfoxide | O↑S | H— | H— | —O—CH$_2$—Ph'—CH=CH$_2$ |
| (g) vinylbenzyl 6-benzoylaminopenicillanate | S | Ph—CO— | H— | —O—CH$_2$—Ph'—CH=CH$_2$ |
| (h) vinylbenzyl 6-benzoylaminopenicillanate sulfoxide | O↑S | Ph—CO— | H— | —O—CH$_2$—Ph'—CH=CH$_2$ |

The optically active monomer of the present invention can be easily prepared from 6-aminopenicillanic acid which is a fermentation product, and an acyl derivative thereof according to procedures of synthetic chemistry (see examples given hereinafter).

Optically Active Polymer

The novel optically active polymer provided according to the present invention is synthesized by homopolymerizing the above-mentioned optically active monomer having a radical-polymerizable group at the 3- or 6-position of the penam nucleus by the radical mechanism or ion mechanism. Radical polymerization conditions customarily adopted can be used for the radical polymerization in the present invention. For example, there may be adopted a process in which the monomer of the present invention is dissolved in a solvent together with a compound capable of forming a free radical by heating or irradiation with ultraviolet rays, such as azobisisobutyronitrile, and the solution is heated or irradiated with ultraviolet rays. Furthermore, radical polymerization can be initiated by generating a free radical from the carbon-to-carbon double bond of the monomer of the present invention by irradiation with ultraviolet rays or the like.

Accordingly, the polymer of the present invention comprises substantially 100 mole% of recurring units formed by cleavage of the ethylenically unsaturated double bond of the group X or Z of the optically active monomer represented by the above-mentioned formula (I). In the case where one carbon atom of the ethylenically unsaturated bond is substituted by two hydrogen atoms and the other carbon atom is substituted by one hydrogen atom, and where the portion of the monomer other than this ethylenically unsaturated bond is expressed as W, the polymer of the present invention has the following recurring units:

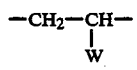

The polymer of the present invention is characterized in that the polymer comprises such recurring units.

Another characteristic feature of the novel polymer is that the number average molecular weight (Mn) is at least 3,000. In this case, the number average molecular weight is determined by GPC (gel permeation chromatography) which is calibrated by using polystyrene standards. Typical Mn is 3,000 to 1,000,000, and typical Mw/Mn is 1.2 to 8.0 where Mw is a weight average molecular weight.

The polymer is characterized in that the polymer has a penam nucleus. It is known that the penam nucleus reacts promptly with various reagents to produce various derivatives. Accordingly, the compound of the present invention can be further chemically modified by utilizing this high reactivity inherent in the penam nucleus. For example, ring-opening addition reaction of an alkylamine to the 4-membered ring and ring-opening addition of an alcohol to the 4-membered ring in the presence of a base catalyst are possible. The compound obtained according to the present invention can be used after it has been subjected to such chemical conversion.

The optically active polymer of the present invention is a homopolymer of a corresponding ethylenically unsaturated monomer as described above. Accordingly, preferred examples of the optically active polymer of the present invention will be obvious to those skilled in the art from the foregoing description. For example, homopolymers of the above-mentioned monomers (a) through (d) set forth in the Table can be mentioned.

The above-mentioned substituents and preparation processes will now be described in detail with respect to the following examples that by no means are intended to limit the scope of the invention.

REFERENTIAL EXAMPLE 1

6-Aminoenicillanic acid (64.9 g, 300 millimoles) was dispersed in dry methylene chloride (1,500 ml) at room temperature in an argon atmosphere, and triethylamine (60.7 g, 600 millimoles) was added to the dispersion with stirring, which was continued until a homogeneous solution was formed. Then, methyl acetoacetate (34.8 g, 300 millimoles) was dropped into the solution, and the mixture was stirred at room temperature for 3 hours and concentrated under a reduced pressure. The remaining oily product was dried under a reduced pressure, and dry N,N-dimethylformamide (700 ml) and benzyl bromide (54.7 g, 320 millimoles) were added thereto, the mixture then being stirred at room temperature for 3 hours. Distilled water (1,000 ml) was added to the mixture, which was subjected to extraction with methylene chloride-diethyl ether (1:5) mixture (4×300 ml), washed with water (2×300 ml) and brine (2×200 ml) and dried over magnesium sulfate. The solvent was removed under a reduced pressure, and the residue was dissolved in dry acetone (750 ml). p-Toluenesulfonic acid monohydrate (68.5 g, 360 millimoles) was added to the solution with stirring, and the mixture was stirred for 12 minutes. Diethyl ether (750 ml) was added to the mixture, and the crystal precipitated was recovered by filtration and washed with diethyl ether two times to obtain 83.7 g (58.2%) of a crude crystal. Recrystallization from a methanol/methylene chloride/diethyl ether mixed solvent gave 74.3 g (51.8%) of a p-toluenesulfonic acid salt of benzyl 6-aminopenicillanate.

Melting point: 156° C.

IR (cm$^{-1}$): 1770, 1725, 1650, 1600

$^1$H-NMR (CDCl$_3$-DMSO-d6), δ(ppm): 9.03 (br, 3H), 7.42 (AB, 4H), 7.38 (s, 5H), 5.52 (d, 1H, J=4.3 Hz), 5.20 (d, 2H, J=1.6 Hz), 4.94 (d, 1H, J=4.3 Hz), 4.49 (s, 1H), 2.35 (s, 3H), 1.65 (s, 3H), 1.40 (s, 3H).

REFERENTIAL EXAMPLE 2

6-Aminopenicillanic acid (43.2 g, 200 millimoles) was dispersed in distilled water at 0° C., and p-toluene-sulfonic acid monohydrate (38.0 g, 200 millimoles) was added to the dispersion with stirring, which was continued at 0° C. until a homogeneous solution was formed. Then, a 40% aqueous solution of peracetic acid (40.0 g, 210 millimoles) was gradually dropped into the solution so that the temperature of the reaction liquid was maintained at 5 to 10° C. After completion of the dropping, the liquid was stirred for 1 hour on an ice bath, and 150 ml of acetone was added to the liquid. The precipitated crystal was recovered by filtration, washed with diethyl ether and dried under a reduced pressure to obtain 56.0 g (69.2%) of a p-toluenesulfonic acid salt of 6-aminopenicillanic acid sulfoxide.

Melting point: 168–170° C.

IR (cm$^{-1}$): 1795, 1720

REFERENTIAL EXAMPLE 3

The p-toluenesulfonic acid salt of 6-aminopenicillanic acid sulfoxide (9.1 g, 22.5 millimoles) synthesized in Referential Example 2 was dispersed in dry methylene chloride (125 ml) at room temperature in an argon atmosphere, and triethylamine (9.4 ml, 67.5 millimoles) was added to the dispersion with stirring, which was continued for about 5 minutes until a homogeneous solution was formed. Then, methyl acetoacetate (2.42 ml, 22.5 millimoles) was dropped into the solution, and the mixture was stirred at room temperature for 3 hours and concentrated under a reduced pressure. The remaining oily product was dried under a reduced pressure, and dry N,N-dimethylformamide (50 ml) and benzyl bromide (22.5 ml, 2.71 millimoles) were added to the oily product, the mixture then being stirred at room temperature for 3 hours. Distilled water (60 ml) was added to the mixture, and the resulting mixture was extracted with methylene chloride-diethyl ether (1:5) (4×60 ml), washed with water (2×50 ml) and brine (2×20 ml) and dried over magnesium sulfate. The solvent was then removed under a reduced pressure. The residue was dissolved in dry acetone (40 ml), and p-toluenesulfonic acid monohydrate (4.28 g, 22.5 millimoles) was added to the solution with stirring. The mixture was stirred for 12 minutes. Diethyl ether (100 ml) was added to the mixture, and the crystal precipitated was recovered by filtration and washed with diethyl ether two times. Recrystallization from a methanol-methylene chloride-diethyl ether mixed solvent gave 3.48 g (31.3%) of a p-toluenesulfonic acid salt of benzyl 6-aminopenicillanate sulfoxide.

Melting point: 154–156° C.

IR (cm$^{-1}$) 1795, 1750, 1590

$^1$H-NMR (CDCl$_3$-DMSO-d6), δ(ppm): 7.45 (AB, 4H), 7.38 (s, 5H), 5.23 (AB, 2H), 5.21 (d, 1H, J=4.7 Hz), 5.13 (d, 1H, J=4.7 Hz), 4.63 (s, 1H), 2.35 (s, 3H), 1.62 (s, 3H), 1.05 (s, 3H)

EXAMPLE 1

6-Aminopenicillanic acid (6.49 g, 30 millimoles) was dispersed in dry methylene chloride (150 ml) at room temperature in an argon atmosphere, and triethylamine (8.4 ml, 60 millimoles) was added to the dispersion with stirring. The mixture was stirred until a homogeneous solution was formed. Then, methyl acetoacetate (3.2 ml, 30 millimoles) was dropped into the solution. The mixture was stirred for 3 hours at room temperature and concentrated under a reduced pressure. The remaining oily product was dried under a reduced pressure, and dry N,N-dimethylformamide (70 ml) and vinylbenzyl chloride (meta-para mixture) (4.58 g, 30 millimoles) were added to the oily product. The mixture was stirred at room temperature for 18 hours. Then, distilled water (60 ml) was added to the mixture, and the resulting mixture was extracted with methylene chloride-diethyl ether (1:5) (4×60 ml), washed with water (2×5 ml) and brine (2×50 ml) and dried over magnesium sulfate. The solvent was removed under a reduced pressure. The residue was dissolved in dry acetone (20 ml), and p-toluenesulfonic acid monohydrate (3.12 g, 16.4 millimoles) was added to the solution with stirring, the mixture then being stirred for 12 minutes. Diethyl ether (50 ml) was added to the mixture, and the crystal precipitated was recovered by filtration and washed with diethyl ether two times. By recrystallization from a methylene chloride-diethyl ether mixed solvent, 4.63 g (30.7%) of a meta-para mixture of a p-toluenesulfonic acid salt of vinylbenzyl 6-aminopenicillanate was obtained.

Melting point: 130.5–131.5° C.

[α]$_D$: 130 (c 1, methanol)

IR (cm$^{-1}$): 1790, 1750, 1625

$^1$H-NMR (CDCl$_3$), δ(ppm): 8.64 (br, 3H), 7.43 (AB, 4H), 7.40–7.22 (m, 4H); 6.69 (dd, 1H, J=17.5, 11Hz), 5.78 and 5.55 (d and 1H as a whole, each J=17.5 Hz), 5.41 (d, 1H, J=4.1 Hz), 5.28 and 5.27 (d and d, 1H as a whole, each J=11 Hz), 5.13 - 5.12 (m, 2H), 4.94 (d, 1H, J=4.1 Hz), 4.45 and 4.44 (s and s, 1H as a whole), 2.31 (s, 3H), 1.43 (s, 3H), 1.29 and 1.28 (s and s, 3H as a whole)

EXAMPLE 2

The p-tol uenesulfonic acid salt of 6-aminopenicillanic acid sulfoxide (8.0 g, 19.8 millimoles) synthesized in Referential Example 2 was dispersed in dry methylene chloride (160 ml) at room temperature in an argon atmosphere, and triethylamine (8.28 ml, 59.4 millimoles) was added to the dispersion with stirring, the mixture being stirred until a homogeneous solution was formed. Then, methyl acetoacetate (2.13 ml, 19.8 millimoles) was dropped into the solution, and the mixture was stirred at room temperature for 3 hours and concentrated under a reduced pressure. The remaining oily product was dried under a reduced pressure, and dry N,N-dimethylformamide (50 ml) and vinylbenzyl chloride (meta-para mixture) (3.02 g, 19.8 millimoles) were added to the oily product, the mixture being stirred at room temperature for 18 hours. Distilled water (70 ml) was added to the mixture, and the resulting mixture was extracted with methylene chloride-diethyl ether (1:5) (4×70 ml), washed with water (2×50 ml) and brine (2×30 ml), and dried over magnesium sulfate. The solvent was removed under a reduced pressure. By using the silica gel column chromatography [gel: 500 ml, chloroform-ethyl acetate (10:1)], a component having an Rf value of 0.32 (1.3 g) at the silica gel thin layer chromatography [chloroform-ethyl acetate (10:1)] was collected, and this fraction was dissolved in dry acetone (4 ml). Then, ptoluenesulfonic acid monohydrate (0.63 g, 3.3 millimoles) was added to the solution with stirring, and the mixture was stirred for 10 minutes. Diethyl ether (80 ml) was added to the mixture, and the crystal precipitated was recovered by filtration and washed with diethyl ether two times. By recrystallization from a methanol-methylene chloride-diethyl ether mixed solvent, 0.76 g (7.4%) of a p-toluenesulfonic acid salt of vinylbenzyl 6-aminopenicillanate sulfoxide was obtained.

Melting point: 164.5°–165.0° C.
$[\alpha]_D$: 118 (c 1, methanol)
IR (cm$^{-1}$): 1790, 1745, 1620
$^1$H-NMR (CDCl$_3$-DMSO-d6), δ(ppm): 8.9 (br, 3H), 7.45 (AB, 4H), 7.44–7.26 (m, 4H), 6.72 (dd, 1H, J=17.5 and 11 Hz), 5.79 and 5.78 (d and d, 1H as a whole, each J=17.5 Hz), 5.31–5.16 (overlaped m, 4H), 5.08 (d, 1H, J=4.6 Hz), 4.64 and 4.62 (s and s, 1H as a whole), 2.35 (s, 3H), 1.64 and 1.63 (s and s, 3H as a whole), 1.09 and 1.08 (s an s, 3H as a whole)

EXAMPLE 3

The p-toluenesulfonic acid salt of benzyl 6-aminopenicillanate (5.00 g, 10.4 millimoles) synthesized in Referential Example 1 was dispersed in methylene chloride (700 ml) at room temperature, and triethylamine (1.82 ml, 13.1 millimoles) was added to the dispersion in an argon atmosphere with stirring. When the liquid became homogeneous, the same amount of triethylamine was further added to the liquid, and the mixture was cooled in an ice bath. A solution of acrylic acid chloride (0.93 ml, 11.4 millimoles) in 250 ml of methylene chloride was dropped into the liquid over a period of 1 hour while the liquid temperature was maintained at 0° to 5° C., and the mixture was stirred at room temperature for 3 hours. The solution obtained was washed with a 5% aqueous solution of sodium bicarbonate (2×100 ml), distilled water (2×100 ml) and brine (50 ml) and dried over magnesium sulfate. The solvent was removed under a reduced pressure. At the silica gel column chromatography [gel: 300 ml, chloroform-ethyl acetate (10:1)], the first effluent component was recovered, and this component was amply dried under a reduced pressure to obtain 2.36 g (62.9%) of benzyl 6-acrylaminopenicillanate.

$[\alpha]_D$: 177 (c 1, methylene chloride)
IR (cm$^{-1}$): 1780, 1746, 1670, 1630
$^1$H-NMR (CDCl$_3$), δ(ppm): 7.41–7.36 (m, 5H), 6.36 (dd, 1H, J=17.0 and 1.0 Hz), 6.24 (d, 1H, J=9 Hz), 6.13 (dd, 1,, J=17.0 and 10.3 Hz), 5.80 (dd, 1H, J=9 and 4.1 Hz), 5.75 (dd, 1H, J=10.3 and 1.0 Hz), 5.57 (d, 1H, J=4.1 Hz), 5.20 (AB, 2H), 4.47 (s, 1H), 1.64 (s, 3H), 1.43 (s, 3H)

EXAMPLE 4

The p-toluenesulfonic acid salt of benzyl 6-aminopenicillanate (5.00 g, 10.4 millimoles) synthesized in Referential Example 1 was dispersed in methylene chloride (700 ml) at room temperature, and triethylamine (1.82 ml, 13.1 millimoles) was added to the dispersion with stirring in an argon atmosphere. When the liquid became homogeneous, the same amount of triethylamine was added to the liquid, and the mixture was cooled in an ice bath. A solution of methacrylic acid chloride (1.11 ml, 11.4 millimoles) in methylene chloride (22 ml) was added dropwise to the mixture while the liquid temperature was maintained at 0° to 5° C., and the mixture was stirred at room temperature for 3 hours. The thus formed solution was washed with a 5% aqueous solution of sodium bicarbonate (2×100 ml), distilled water (3×100 ml) and brine (2×20 ml) and dried over magnesium sulfate, and the solvent was removed under a reduced pressure. At the silica gel column chromatography gel: 300 ml, chloroform-ethyl acetate (10:1)], a component having an Rf value of 0.88 at. the silica gel thin layer chromatography [methylene chloride-ethyl acetate (1:1)] was collected, and the component was amply dried under a reduced pressure to obtain 3.72 g (95.6%) of benzyl 6-methacrylaminopenicillanate.

$[\alpha]_D$: 154 (c 1, methylene chloride)
IR (cm$^{-1}$]: 1795, 1750, 1670
$^1$H-NMR (CDCl$_3$), δ(ppm): 7.37 (s, 5H), 6.44 (d, 1H, J=9 Hz), 5.76 (d, 1H, J=0.8 Hz), 5.74 (dd, 1H, J=9 and 4.1 Hz), 5.57 (d, 1H, J=4.1 Hz), 5.43–5.42 (m, 1H), 5.20 (d, 2H, J=0.8 Hz), 4.48 (s, 1H), 1.98 (s, 3H), 1.64 (s, 3H), 1.43 (s, 3H)

EXAMPLE 5

The p-toluenesulfonic acid salt of benzyl 6-aminopenicillanate sulfoxide (0.261 g, 0.528 millimole) synthesized in Referential Example 3 was dispersed in methylene chloride (30 ml) at room temperature, and triethylamine (0.184 ml, 1.32 millimoles) was added to the dispersion with stirring at room temperature. The mixture was then cooled in an ice bath. A solution of acrylic acid chloride (0.0472 ml, 0.581 millimole) in 10 ml of methylene chloride was added dropwise to the liquid over a period of 1 hour while the liquid temperature was maintained at 0° to 5° C., and the mixture was stirred at room temperature for 3 hours. The thus formed solution was washed with a 5% aqueous solution of sodium bicarbonate (2×50 ml), distilled water (2×50 ml) and brine (30 ml) and dried over magnesium sulfate, and the solvent was removed under a reduced pressure. At the silica gel column chromatography [gel: 50 ml, chloroformethyl acetate (10:1)], a component having an Rf value of 0.22 at the silica gel thin layer chromatography [methylene chloride-ethyl acetate (5:1)] was collected, and this component was amply dried under a reduced pressure to obtain 0.181 g (91.0%) of benzyl 6-acrylaminopenicillanate sulfoxide.

$[\alpha]_D$: 193 (c 1, methylene chloride)
IR (cm$^{-1}$) 1790, 1750, 1680, 1630
$^1$H-NMR (CDCl$_3$), δ(ppm): 7.39 (s, 5H), 7.15 (d, 1H, J=10.3 Hz), 6.33 (dd, 1H, 17.2 and 1.0 Hz), 6.15 (dd, 1H, J=10.3 and 4.6 Hz), 6.09 (dd, 1H, J=17.2 and 10.3 Hz), 5.75 (dd, 1H, J=10.3 and 1.0 Hz), 5.24 (AB, 2H), 5.05 (d, 1H, J=4.6 Hz), 4.70 (s, 1H), 1.68 (s, 3H), 1.09 (s, 3H)

EXAMPLE 6

The p-toluenesulfonic acid salt of benzyl 6-aminopenicillanate sulfoxide (5.14 g, 10.4 millimoles) synthesized in Referential Example 3 was dispersed in methylene chloride (700 ml) at room temperature, and triethylamine (1.82 ml, 13.1 millimoles) was added to the dispersion with stirring in an argon atmosphere. When the liquid became homogeneous, the same amount of triethylamine was added, and the mixture was cooled in an ice bath. A solution of methacrylic acid chloride (1.11 ml, 11.4 millimoles) in 200 ml of methylene chloride was dropped into the liquid over a period of 1 hour while the liquid temperature was maintained at 0° to 5° C., and the mixture was stirred at room temperature for 3 hours. The thus formed solution was washed with a 5% aqueous solution of sodium bicarbonate (2×100 ml), distilled water (3×100 ml) and brine (2×20 ml) and dried over magnesium sulfate, and the solvent was removed under a reduced pressure. At the silica gel column chromatography [gel: 300 ml, chloroform-ethyl acetate (15:1)], a component having an R value of 0.51 at the silica gel thin layer chromatography [methylene chloride-ethyl acetate (5:1)] was collected, and this component was amply dried under a reduced pressure to obtain 3.42 g (84.2%) of benzyl 6-methacrylaminopenicillanate sulfoxide.

Melting point: 135°–136° C.
$[\alpha]_D$: 187 (c 1, methylene chloride)
IR (cm$^{-1}$): 1780, 1750, 1670, 1625
$^1$H-NMR (CDCl$_3$), δ(ppm): 7.45 (d, 1H, J=10 Hz), 7.39 (s, 5H), 6.13 (dd, 1H, 10 and 4.6 Hz), 5.79 (d, 1H, J=0.8 Hz), 5.43 (m, 1H), 5.24 (AB, 2H), 5.05 (d, 1H, J=4.6 Hz), 4.70 (s, 1H), 1.96–1.95 (m, 3H), 1.68 (s, 3H), 1.09 (s, 3H)

EXAMPLE 7

The p-toluenesulfonic acid salt of vinylbenzyl 6-aminopenicillanate (meta-para mixture) (1.04 g, 2.06 millimoles) synthesized in Example 1 was dissolved in methylene chloride (150 ml) at room temperature, and triethylamine (0.72 ml, 5.15 millimoles) was added to the solution with stirring in an argon atmosphere. The mixture was then cooled in an ice bath. A solution of benzoyl chloride (0.26 ml, 2.23 millimoles) in 40 ml of methylene chloride was dropped into the liquid over a period of 1 hour while the liquid temperature was maintained at 0° to 5° C., and the mixture was stirred at room temperature for 3 hours. The thus formed solution was washed with a 5% aqueous solution of sodium bicarbonate (2×100 ml), distilled water (3×100 ml) and brine (50 ml) and dried over magnesium sulfate, and the solvent was removed under a reduced pressure. At the silica gel column chromatography (gel: 80 ml, chloroform), a component having an Rf value of 0.89 at the silica gel thin layer chromatography [methylene chloride-ethyl acetate (5:1)] was collected, and this component was amply dried under a reduced pressure to obtain 0.836 g (93.0%) of a meta-para mixture of vinylbenzyl 6-benzoylaminopenicillanate.

$[\alpha]_D$: 151 (c 1, methylene chloride)
IR (cm$^{-1}$): 1785, 1750, 1665, 1605
$^1$H-NMR (CDCl$_3$), δ(ppm): 7.80–7.28 (m, 9H), 6.78 (d, 1H, J=9.0 Hz), 6.72 (dd, 1H, J=17.7 .ah.d 10.8 Hz), 5.90 and 5.90 (dd and dd, 1H as a whole, each J=9.0 and 4.1 Hz), 5.78 (d, 1H, J=17.7 Hz), 5.64 and 5.64 (d and d, 1H as a whole, each J=4.1 Hz), 5.30 and 5.29 (d and d, 1H as a whole, each J=10.8 Hz), 5.21–5.19 (m, 2H), 4.52 and 4.51 (s and s, 1H as a whole), 1.67 and 1.66 (s and s, 3H as a whole), 1.46 and 1.44 (s and s, 3H as a whole)

EXAMPLE 8

The p-toluenesulfonic acid salt of vinylbenzyl 6-aminopenicillanate sulfoxide (meta-para mixture) (0.505 g, 0.970 millimole) synthesized in Referential Example 3 was dispersed in methylene chloride (70 ml) at room temperature, and triethylamine (0.169 ml, 1.21 millimoles) was added to the dispersion with stirring in an argon atmosphere. The mixture was stirred at room temperature for 10 minutes, and the same amount of triethylamine was added thereto. The mixture was then cooled in an ice bath. A solution of benzoyl chloride (0.124 ml, 1.07 millimoles) in 20 ml of methylene chloride was added dropwise to the liquid over a period of 1 hour while the liquid temperature was maintained at 0° to 5° C., and the mixture was stirred at room temperature for 3 hours. The thus formed solution was washed with a 5% aqueous solution of sodium bicarbonate (2×50 ml), distilled water (3×50 ml) and brine (20 ml) and dried over magnesium sulfate, and the solvent was removed under a reduced pressure. At the silica gel column chromatography (gel: 50 ml, chloroform), a component having an Rf value of 0.55 at the silica gel thin layer chromatography [methylene chloride-ethyl acetate (5:1)] was collected, and this component was amply dried under a reduced pressure to obtain 0.328 g (74.7%) of a meta-para mixture of vinylbenzyl 6-benzoylaminopenicillanate sulfoxide.

$[\alpha]_D$: 150 (c 1 methylene chloride)
IR (cm$^{-1}$): 1780, 1745, 1670, 1605
$^1$H-NMR (CDCl$_3$), δ(ppm): 7.86 (d, 1H, J=10 Hz), 7.80.–7.27 (m, 9H), 6.72 (dd, 1H, J=17.7 and 11 Hz), 6.30 (dd, 1H, J=10 and 4.6 Hz), 5.78 (d, 1H, J=17.7 Hz), 5.32–5.28 (m, 2H), 5.19 and 5.17 (d and d, 1H as a whole, each J=11 Hz), 5.12 and 5.11 (d and d, 1H as a whole, each J=4.6 Hz), 4.75 and 4.74 (s and s, 1H as a whole), 1.70 and 1.69 (s and s, 3H as a whole), 1.13 and 1.12 (s and s, 3H as a whole)

EXAMPLE 9

Potassium penicillin G (5.59 g, 15.0 millimoles) was dispersed in N,N-dimethylformamide (30 ml) at room temperature, and vinylbenzyl chloride (meta-para mixture) (2.08 g, 13.6 millimoles) was dropped into the dispersion over a period of 30 minutes. The mixture was stirred at room temperature for 2 hours, and distilled water (50 ml) was added to the mixture. The resulting mixture was extracted with methylene chloride-diethyl ether (1:5) (4×50 ml), washed with distilled water (2×20 ml), a 5% aqueous solution of oxalic acid (2×20 ml), distilled water (20 ml), a 5% aqueous solution of sodium bicarbonate (2×20 ml), distilled water (20 ml) and brine (2×20 ml) and dried over magnesium sulfate. The solvent was removed under a reduced pressure and the residue was dried under a reduced pressure to obtain 2.37 g (38.7%) of a meta-para mixture of vinylbenzyl 6-phenylacetaminopenicillanate.

$[\alpha]_D$: 122 (c 1, methylene chloride)
IR (cm$^{-1}$): 1780, 1745, 1670, 1605
$^1$H-NMR (CDCl$_3$), δ(ppm): 7.41–7.27 (m, 9H), 6.70 (dd, 1H, J=17.5 and 11.0 Hz), 6.08 (d, 1H, J=9.2 Hz), 5.77 and 5.76 (dd and dd, 1H as a whole, each J=17.5 and 0.8 Hz), 5.64 and 5.63 (dd and dd, 1H as a whole, former J=9.2 and 6.6 Hz, latter J=9.2 and 4.1 Hz), 5.50 and 5.49 (d and d, 1H as a whole, former J=4.4 Hz, latter J=4.1 Hz), 5.28 (d, 1H, J=11.0 Hz), 5.15 (d, 2H, J=6.2 Hz), 4.40 and 4.39 (s and s, 1 H as a whole), 3.63 (s, 2H), 1.40 and 1.39 (s and s, 3H as a whole), 1.37 and 1.35 (s and s, 3H as a whole)

EXAMPLE 10

Benzyl 6-acrylaminopenicillanate (0.400 g, 1.11 millimoles) synthesized i n Example 3 and azobisisobutyronitrile (3.0 mg, 0.022 millimole) were dissolved in methylene chloride (1 ml), and the solution was deaerated and sealed in a glass ampoule. The solution was irradiated with rays from a high-pressure mercury lamp in a water bath maintained at 35° C. for 7 hours, and the ampoule was opened and 1 ml of methylene chloride was added to the content. The mixture was poured into methanol (120 ml), and the precipitate was recovered by filtration and dried under a reduced ressure to obtain 0.220 g (55.0%) of a resin.

$[\alpha]_D$: 178 (c 1, methylene chloride)

IR (cm$^{-1}$): 1780, 1745, 1680

Molecular weight (GPC, calibrated by using polystyrene standards): Mn=9760, Mw/Mn =1.81.

EXAMPLE 11

Benzyl 6-acrylaminopenicillanate (0.420 g, 1.17 millimoles) synthesized in Example 3 and azobisisobutyronitrile (3.0 mg, 0.022 millimole) were dissolved in methylene chloride (1 ml), and the solution was deaerated and sealed in a glass ampoule. The solution was heated on an oil bath maintained at 60° C. for 20 hours. The ampoule was opened, and 1 ml of methylene chloride was added to the content. The mixture was poured into methanol (100 ml), and the precipitate was recovered by filtration and dried under a reduced pressure to obtain 0.120 g (28.6%) of a resin.

$[\alpha]_D$: 192 (c 1, methylene chloride)

IR (cm$^{-1}$): 1780, 1745, 1680

Molecular weight (GPC, calibrated by using polystyrene standards): Mn=7000, Mw/Mn=1.62

EXAMPLE 12

Benzyl 6-acrylaminopenicillanate sulfoxide (48 mg, 0.23 millimole) synthesized in Example 5 and azobisisobutyronitrile (0.27 mg, 1.6 μmoles) were dissolved in methylene chloride (0.255 ml), and the solution was deaerated and sealed into a glass ampoule. The solution was heated on an oil bath maintained at 50° C. for 48 hours. The ampoule was opened, and 2 ml of methylene chloride was added to the content. The insoluble substances were discarded, and the solution was poured into methanol (50 ml). The precipitate was recovered by filtration and dried under a reduced pressure to obtain 36 mg (75%) of a resin.

$[\alpha]_D$: 200 (c 1, methylene chloride)

IR (cm$^{-1}$): 1785, 1750, 1670

Molecular weight (GPC, calibrated by using polystyrene standards): Mn=6740, Mw/Mn=2.83.

EXAMPLE 13

Benzyl 6-methacrylaminopenicillanate sulfoxide (391 mg, 1.00 millimole) synthesized in Example 6 and azobisisobutyronitrile (2.2 mg, 0.013 millimole) were dissolved in methylene chloride (2.0 ml), and the solution was deaerated and sealed in a glass ampoule. The solution was heated on an oil bath maintained at 50° C. for 48 hours. The ampoule was opened, and 5 ml of methylene chloride was added to the content. The mixture was then poured into methanol (50 ml). The precipitate was recovered by filtration and dried under a reduced pressure to obtain 357 mg (91.3%) of a resin.

$[\alpha]_D$: 217 (c 1, methylene chloride)

IR (cm$^{-1}$) 1795, 1750, 1675

Molecular weight (GPC, calibrated by using polystyrene standards): Mn=70300, Mw/Mn=2.63

EXAMPLE 14

Vinylbenzyl 6-(phenylacatamino)penicillanate (577 mg, 1.28 millimoles) synthesized in Example 9 and azobisisobutyronitrile (2.1 mg, 13 μmoles) were dissolved in 1,4-dioxane (2.2 ml), and the solution was deaerated and sealed in a glass ampoule. The solution was heated on an oil bath maintained at 70° C. for 24 hours. The ampoule was opened, and 3 ml of 1,4-dioxane was added to the content. The mixture was poured into methanol (200 ml), and the precipitate was recovered by filtration and dried under a reduced pressure to obtain 512 mg (90.3%) of a resin.

$[\alpha]_D$: 150 (c 1, methylene chloride)

IR (cm$^{-1}$) 1795, 1725, 1660, 1605

Molecular weight (GPC, calibrated by using polystyrene standards): Mn=16700, Mw/Mn=2.49

What is claimed is:

1. An optically active polymer having a number of average molecular weight of at least 3000 and comprising substantially 100 mole % of recurring units formed by cleavage of the ethylenically unsaturated bond of the group X or Z of an optically active, ethylenically unsaturated monomer represented by the following structural formula:

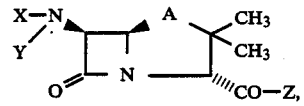

wherein: A stands for S, SO or SO$_2$, X and Y each stand for a hydrogen atom or a substituent selected from the group consisting of alkyl groups and acyl groups; Z stands for a substituent selected from the group consisting of alkoxy, alkylamino, hydroxyl and silyoxy groupsl; and X and Y can be bonded together to form a ring with the nitrogen atom to which they are bonded or X and Y can be a single group bonded to said nitrogen atom through a double bond, with the proviso that at least one of X and Z is an alkenyl equivalent to said group and that, when X is the alkenyl equivalent it is acryloyl or methacryloyl group and H is a hydrogen atom.

2. An optically active polymer as set forth in claim 1 wherein, when X or Y of the optically active, ethylenically unsaturated monomer stands for an alkyl or acyl group, it has 1 to 30 carbon atoms.

3. An optically active polymer as set forth in claim 2 wherein X or Y of the optically active, ethylenically unsaturated monomer has 1 to 15 carbon atoms.

4. An optically active polymer as set forth in claim 1 wherein Z of the optically active, ethylenically unsaturated monomer stands for an alkoxy, alkylamino or silyloxy group, Z has 1 to 30 carbon atoms.

5. An optically active polymer as set forth in claim 4 wherein Z has 1 to 20 carbon atoms.

6. An optically active polymer as set forth in claim 1 wherein X of the optically active, ethylenically unsaturated monomer stands for an acyl group, and Y of the optically active, ethylenically unsaturated monomer stands for a hydrogen atom.

7. An optically active polymer as set forth in claim 6 wherein the acyl group is an acryloyl, methacryloyl, phenylacetyl or benzoyl group.

8. An optically active polymer as set forth in claim 1 wherein Z of the optically active, ethylenically unsaturated monomer stands for an alkoxy group.

9. An optically active polymer as set forth in claim 8 wherein the alkoxy group is a benzyloxy or vinylbenzyloxy group.

10. An optically active polymer as set forth in claim 1 wherein A of the optically active, ethylenically unsaturated monomer is S or SO.

11. An optically active polymer as set forth in claim 1 wherein only one of X and Z has an ethylenically unsaturated bond.

12. An optically active polymer as set forth in claim 1 wherein the optically active, ethylenically unsaturated monomer is selected from (a) benzyl 6-acrylaminopenicillanate, (b) benzyl 6-acrylaminopenicillanate sulfoxide, (c) benzyl 6-methacrylaminopenicillanate sulfoxide and (d) vinylbenzyl 6-phenylacetaminopenicillanate.

13. An optically active polymer as set forth in claim 1 wherein the optically active, ethylenically unsaturated monomer is selected from the group consisting of (e) vinylbenzyl 6-aminopenicillanate, (f) vinylbenzyl benzoylaminopenicillanate, and (h) vinylbenzyl 6-benzoylaminopenicillanate sulfoxide.

14. An optically active polymer as set forth in claim 11 wherein in the optically active, ethylenically unsaturated monomer is benzyl 6-methacrylaminopenicillanate sulfoxide and wherein A stands for a sulfoxide, X stands for a methacrylol group, Y stands for a hydrogen atom and Z stands for a benzyloxy group.

* * * * *